(12) United States Patent
Gat et al.

(10) Patent No.: US 8,858,994 B2
(45) Date of Patent: Oct. 14, 2014

(54) PHARMACEUTICAL FORMULATION COMPRISING EZETIMIBE

(75) Inventors: Ganesh Gat, Pune (IN); Pasupuleti Giridhara Rao, Nellore (IN); Javed Hussain, Aurangabad (IN)

(73) Assignee: Ratiopharm GmbH, Ulm (DE)

( * ) Notice: Subject to any disclaimer, the term of this patent is extended or adjusted under 35 U.S.C. 154(b) by 464 days.

(21) Appl. No.: 12/747,270

(22) PCT Filed: Dec. 9, 2008

(86) PCT No.: PCT/EP2008/010431
§ 371 (c)(1),
(2), (4) Date: Jul. 21, 2010

(87) PCT Pub. No.: WO2009/074286
PCT Pub. Date: Jun. 18, 2009

(65) Prior Publication Data
US 2010/0291207 A1  Nov. 18, 2010

(30) Foreign Application Priority Data
Dec. 10, 2007 (IN) .......................... 2579/DEL/2007

(51) Int. Cl.
*A61K 45/00* (2006.01)
*A61K 45/06* (2006.01)
*A61K 9/20* (2006.01)
*A61K 31/397* (2006.01)

(52) U.S. Cl.
CPC .............. *A61K 9/2018* (2013.01); *A61K 9/2095* (2013.01); *A61K 31/397* (2013.01); *A61K 9/2059* (2013.01)
USPC ............................ 424/465; 514/460; 514/548

(58) Field of Classification Search
USPC ........................................................ 424/465
See application file for complete search history.

(56) References Cited

U.S. PATENT DOCUMENTS

2006/0160785 A1* 7/2006 Aronhime et al. ........ 514/210.02
2007/0026062 A1* 2/2007 Holm et al. ................... 424/451
2007/0275052 A1* 11/2007 Mahajan et al. .............. 424/451

FOREIGN PATENT DOCUMENTS

| WO | WO 95/08532 A | 3/1995 |
|---|---|---|
| WO | WO 2006/060808 | 6/2006 |
| WO | WO 2007/103453 A | 9/2007 |
| WO | WO 2008/032338 | 3/2008 |

OTHER PUBLICATIONS

Subhadhirasakul et al., Drug Development and Industrial Pharmacy, 27(1), 81-87, published 2001 by Marcel Dekker, Inc.*
Hill, Journal of Pharmaceutical Sciences, 65(11), 1694-1696, published Nov. 1976 by Wiley.*
"Zeitz (Ezetimibe) Tablets," Internet Citation, Retrieved from the Internet, URL: http://www.fda.gov/eder/foi/label/2002/21451b1.pdf (retrieved on Jul. 28, 2006).
Chaumeil, J. "Micronization: A Method of Improving the Bioavailability of Poorly Soluble Drugs," Methods and Findings in Experimental and Clinical Pharmacology, vol. 20 (3), pp. 211-215 (Apr. 1998).
Decision of the Board of Appeal of the European Patent Office in Case No. T 0637/09-3.3.02 regarding EP Application No. 01900579.2 to Bayer Pharma Aktiengesellchaft, Laboratorios Leon Farma S.A., opponent, dated Mar. 20, 2013.
Neutral Citation No. [2011] EWHC 1591 (Pat), Claim No. HC10O02910, Judgment of the Honorable Justice Floyd in the High Court of Justice, Chancery Division Patents Court, Royal Courts of Justice, London, England, between Cephalon, Inc. et al. and Orchid Europe Limited, et al., dated Jun. 24, 2011.

* cited by examiner

*Primary Examiner* — Johann R Richter
*Assistant Examiner* — Yanzhi Zhang
(74) *Attorney, Agent, or Firm* — Chalin A. Smith; Smith Patent

(57) ABSTRACT

The present invention relates to novel formulations comprising ezetimibe as active ingredient. In particular the invention relates to a pharmaceutical composition comprising 5 to 20 wt-% ezetimibe, 50 to 85 wt-% diluent, 3 to 25 wt-% disintegrant, 1 to 10 wt-% binder, and 0.5 to 1 wt-% lubricant, characterized in that the ezetimibe has a particle size distribution of d(0.9) of 5 μm to 35 μm and d(0.5) of 3 μm to 20 μm, as well as methods for preparing said formulations.

24 Claims, No Drawings

PHARMACEUTICAL FORMULATION COMPRISING EZETIMIBE

This application corresponds to the national phase of International Application No. PCT/EP2008/010431 filed Dec. 9, 2008, which, in turn, claims priority to Indian Patent Application No. 2579/DEL/2007 filed Dec. 10, 2007, the contents of which are incorporated by reference herein in their entirety.

FIELD OF THE INVENTION

The present invention relates to novel formulations comprising ezetimibe as active agent.

BACKGROUND OF THE INVENTION

The compound ezetimibe belongs to a class of lipid-lowering compounds that selectively inhibit the intestinal absorption of cholesterol and related phytosterols.

It is reported that ezetimibe has a mechanism of action that differs from those of other classes of cholesterol-reducing compounds, such as HMG-CoA reductase inhibitors, bile acid sequestrants (resins), fibric acid derivatives, and plant stanols. Ezetimibe reportedly does not inhibit cholesterol synthesis in the liver or increase bile acid excretion. Instead, it appears that ezetimibe localizes and acts at the brush border of the small intestine and inhibits the absorption of cholesterol, leading to a decrease in the delivery of intestinal cholesterol to the liver. The result is a reduction of hepatic cholesterol stores and an increase in clearance of cholesterol from the blood. Such a mechanism is complementary to that of HMG-CoA reductase inhibitors.

Ezetimibe is sold in the US under the brand name Zetia®, which is available as a tablet for oral administration containing 10 mg of ezetimibe and the following inactive ingredients: croscarmellose sodium NF, lactose monohydrate NF, magnesium stearate NF, microcrystalline cellulose NF, povidone USP, and sodium lauryl sulfate NF.

WO 2006/060808 A1 describes ezetimibe polymorphs and processes for preparing same. In particular, this reference describes processes for preparing crystalline forms of ezetimibe, such as ezetimibe form A or form B by precipitating ezetimibe from selected solvents. The micronized ezetimibe particles of WO 2006/060808 have a small particle size and a high specific surface area.

EP 1 353 696 B1 describes a specific composition comprising 10% ezetimibe, 55% lactose monohydrate, 20% microcrystalline cellulose NF, 4% povidone USP, 8% croscarmellose sodium NF, 2% sodium lauryl sulfate and 1% magnesium stearate. The composition of EP 1 353 696 B1 does not contain starch and does not contain starch paste.

WO 95/08532 A1 and WO 95/35277 A1 disclose substituted acetidinone compounds useful as hypocholesterolemic agents. Both documents disclose a composition comprising active compound, lactose, corn starch as a 10% paste in purified water, corn starch and magnesium stearate. However, the amount of active compound in the compositions of these documents is greater than 30 wt-%, and the concentration of lactose is less than 50%.

It is desirable that the ezetimibe containing pharmaceutical compositions show a rather fast dissolution and optionally quick disintegration. It is an object of this invention to provide ezetimibe containing compositions having favourable properties.

SUMMARY OF THE INVENTION

The present invention relates to a pharmaceutical composition comprising 5 to 20 wt-% ezetimibe,
50 to 85 wt-% diluent,
3 to 25 wt-% disintegrant,
1 to 10 wt-% binder, and
0.5 to 1 wt-% lubricant characterized in that the ezetimibe has a particle size distribution of d(0.9) of 5 µm to 80 µm and d(0.5) of 3 µm to 50 µm. Preferably, the ezetimibe has a specific surface area of less than 5 $m^2/g$.

In a preferred embodiment, the pharmaceutical composition of the invention further comprises 0-5 wt-%, preferably 2-5 wt-% solubility enhancer.

Another aspect of the invention is a process for the manufacture of a medicament, said process comprising:
a) providing ezetimibe having a particle size distribution of d(0.9) of 5 µm to 80 µm and d(0.5) of 3 µm to 50 µm, and optionally a specific surface area of less than 5 $m^2/g$;
b) preparing a blend comprising said ezetimibe and one or more pharmaceutically acceptable excipients;
c) optionally granulating the blend; and
d) processing the blend into a composition, preferably into a tablet.

Yet another aspect of this invention is the use of ezetimibe as defined herein for the manufacture of a medicament having a dissolution profile as determined according to WO95/08532 such that at least 90% of ezetimibe are released within 30 minutes.

Another aspect of the invention is the use of ezetimibe for the manufacture of a medicament as defined herein. Yet another aspect of the invention is the use of corn starch and corn starch paste for the manufacture of a medicament comprising ezetimibe, said medicament showing a dissolution of at least 90% of active agent within 30 minutes.

DETAILED DESCRIPTION OF THE INVENTION

The chemical name of ezetimibe is 1-(4-fluorophenyl)-3 (R)-[3-(4-fluorophenyl)-3(S)-hydroxypropyl]-4(S)-(4-hydroxyphenyl)-2-azetidinone. The structural formula is:

The term "ezetimibe", as used herein, includes any pharmaceutically acceptable salts and solvates of the above compound.

The ezetimibe in accordance with the present invention is characterized by a specific particle size distribution. Preferably, the ezetimibe that is used for manufacturing the pharmaceutical composition of the invention and/or that is present in said pharmaceutical composition has a d(0.9) value of at least 5 µm, preferably at least 7 µm, more preferably at least 9 µm and most preferably at least 10 µm. The upper limit of the d(0.9) value is usually 80 µm, preferably 70 µm, more preferably 35 µm and most preferably 20 µm. The d(0.5) value is preferably at least 3 µm, preferably at least 4 µm, more preferably at least 5 µm, and most preferably at least 6 µm. The upper limit of the d(0.5) value is usually 50 µm, preferably 20 µm, more preferably 15 µm and most preferably 10 µm. A preferred range of the d(0.9) value is for example from 5 µm to 35 µm, more preferably from 7 µm to 20 µm. Other possible ranges of the d(0.9) value are from 9 µm to 80 µm and from 10 µm to 70 µm. A preferred range of the d(0.5) value is for example from 3 µm to 20 µm, more preferably from 4 µm to 10 µm. Other possible ranges of the d(0.5) value are from 4 µm to 50 µm, from 5 µm to 50 µm and from 6 µm to 15 µm. In a first embodiment, the ezetimibe used in accordance with this invention has a particle size distribution of d(0.9) of 5 µm to 35 µm and d(0.5) of 3 µm to 20 µm. In a more preferred embodiment, the ezetimibe used in accordance with this invention has a particle size distribution of d(0.9) of 7 µm to 20 µm and d(0.5) of 4 µm to 10 µm.

The terms "d(0.9)" and "d(0.5)" as used herein denote that 90% and 50%, respectively, of the particles in a population of particles are smaller than the specified size.

The size of a particle can be determined by any of the methods commonly known in the art. The following methods, for example, may be used: sieves, sedimentation, electrosone sensing (coulter counter), microscopy, low angle laser light scattering. The preferred method for the present invention is laser diffraction or microscope observation. Most preferred are the methods used in the Examples of this application, e.g. the "Wet powder method" as described in Example 5b).

The ezetimibe in accordance with the invention preferably has a specific surface area of less than 5 $m^2/g$, more preferably less than 4 $m^2/g$, more preferably less than 3 $m^2/g$. The specific surface area of the ezetimibe particles of the invention may range from 0.1-4 $m^2/g$, preferably from 0.5-3 $m^2/g$, more preferably from 0.75-2 $m^2/g$, most preferably it will be in the range of from 1-1.5 $m^2/g$.

The specific surface area is determined by Coulter instrument using BET calculation.

One advantage of the pharmaceutical composition of the present invention is that it has a favourable dissolution profile. The dissolution profile is preferably determined as described in Example 2, i.e. using a USP standard apparatus in 500 ml of 1% sodium lauryl sulfate in pH 4.5 phosphate buffer at 50 rpm. Alternatively, the dissolution profile may be determined by the method specified in WO95/08532.

The pharmaceutical formulation preferably shows an in vitro release of at least 80%, more preferably of at least 90%, still more preferably of at least 95%, most preferably of at least 99% of ezetimibe within 30 minutes.

The pharmaceutical composition of this invention may further show favourable disintegration properties. For example, the disintegration time of the composition (preferably a tablet) may be less than 180 seconds, preferably less than 120 seconds, most preferably less than 60 seconds, e.g. 30 to 60 seconds.

The pharmaceutical composition of this invention may be a tablet. The tablet hardness may range from about 15 N to about 70 N, preferably from about 20 N to about 50 N, more preferably from about 20 N to about 40 N, even more preferably from about 25 N to about 45 N and most preferably from about 35 N to about 45 N.

Pharmaceutical compositions of the present invention can optionally be mixed with other forms of ezetimibe and/or other active ingredients such as HMG-CoA reductase inhibitors. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, solubility enhancers and the like. The pharmaceutical compositions of the present invention can further comprise one or more pharmaceutical acceptable carriers, one or more excipients and/or one or more additives. The amount of excipient or additive can range from about 10 to about 95 wt-%, preferably from about 80 to about 95 wt-% of the total weight of the composition or therapeutic combination. One skilled in the art would understand that the amount of carrier(s), excipients and additives can vary.

The pharmaceutical composition of the invention comprises about 50 to about 85% by weight, preferably about 50 to about 75% of diluent. Diluents increase the bulk of a solid pharmaceutical composition and can make a pharmaceutical dosage form containing the composition easier for the patient and care giver to handle. Diluents include cellulose derivatives, sugar derivatives, starch derivatives, calcium phosphate, oxides/corbonates/sulfates/chlorides of magnesium or calcium or sodium etc. Diluents for solid compositions include, for example, microcrystalline cellulose (e.g., Avicel®), Microcelac® (75% lactose monohydrate and 25% microcrystalline cellulose), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, lactose monohydrate, magnesium carbonate, magnesium oxide, maltodextrin, mannitol, polymethacrylates (e.g., Eudragit®), potassium chloride, powdered cellulose, spray dried lactose, sodium chloride, sorbitol and talc.

Carriers for use in the pharmaceutical compositions may include, but are not limited to, lactose, white sugar, sodium chloride, glucose, urea, starch, calcium carbonate, kaolin, crystalline cellulose, silicic acid, and the like.

The pharmaceutical composition of the invention comprises about 1 to about 10 wt-%, preferably 2 to 8% of binder. Binders help bind the active ingredient and other excipients together after compression. Binders include cellulose derivatives, sugar derivatives, starch derivatives, gelatin, guar gum, magnesium aluminium silicate, sodium alginate, stearic acid, hydrophylic or hydrophobic polymers etc. Binders for solid pharmaceutical compositions include for example acacia, alginic acid, carbomer (e.g. carbopol), carboxymethylcellulose sodium, copovidone (Plasdone® S-630), dextrin, ethyl cellulose, gelatin, guar gum, hydrogenated vegetable oil, hydroxyethyl cellulose, hydroxypropyl cellulose, hydroxypropyl methyl cellulose, liquid glucose, magnesium aluminum silicate, maltodextrin, methylcellulose, polymethacrylates, polyvinyl pyrrolidone (PVP), pregelatinized starch, sodium alginate and starch.

The pharmaceutical composition of the invention comprises about 3 to about 25 wt-%, preferably about 5 to about 20 wt-% of disintegrant. Disintegrants can increase dissolution. Disintegrants include cellulose derivatives, hydrophilic polymers, calcium phosphate, alginic acid, colloidal silicon dioxide, starch, sodium starch glycolate, aluminium silicates, guar gum etc. Disintegrants include, for example, alginic acid, carboxymethylcellulose calcium, carboxymethylcellulose sodium, colloidal silicon dioxide, croscarmellose sodium, crospovidone, guar gum, magnesium aluminum silicate, methyl cellulose, microcrystalline cellulose, polacrillin potassium, polyvinyl polypyrrolidone (PVPP, crosslinked polyvinyl pyrrolidone, Polyplasdon® XL 10), powdered cellulose, pregelatinized starch, sodium alginate, sodium starch glycolate and starch.

The pharmaceutical composition of the invention may comprise about 0-5 wt-%, preferably about 2 to 5 wt-% of solubility enhancer. Solubility enhancers increase solubility of Ezetimibe. Solubility enhancers may include, but are not limited to sodium lauryl sulphate, alkalizing agents such as meglumine (D-(−)-N-methylglucamine) and the like.

Disintegration inhibitors may include, but are not limited to, white sugar, stearin, coconut butter, hydrogenated oils, and the like.

Absorption accelerators may include, but are not limited to, quaternary ammonium base and the like. Wetting agents may include, but are not limited to, glycerin, starch, and the like. Adsorbing agents used include, but are not limited to, starch, lactose, kaolin, bentonite, colloidal silicic acid, and the like.

The pharmaceutical composition of the invention comprises about 0.5 to about 1 wt-% of lubricant. A lubricant can be added to the composition to reduce adhesion and ease release of the product from a punch or dye during tableting. Lubricants include glyceryl derivatives, oils, sodium or magnesium stearyl fumarate, stearic acid, calcium or magnesium stearate, talc etc. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium stearyl fumarate, stearic acid, talc and zinc stearate. Glidants can be added to improve the flowability of non-compacted solid composition and improve the accuracy of dosing. Excipients that can function as glidants include for example colloidal silicon dioxide, magnesium trisilicate, powdered cellulose, starch, talc and tribasic calcium phosphate.

Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid.

Tablets can be further coated with commonly known coating materials such as sugar coated tablets, gelatin film coated tablets, tablets coated with enteric coatings, tablets coated with films, double layered tablets, and multi-layered tablets. Capsules can be coated with shell made, for example, from gelatin and optionally contain a plasticizer such as glycerin and sorbitol, and an opacifying agent or colorant.

Solid and liquid compositions can also be dyed using any pharmaceutically acceptable colorant to improve their appearance and/or facilitate patient identification of the product and unit dosage level.

In liquid pharmaceutical compositions of the present invention, the ezetimibe forms described herein and any other solid ingredients are dissolved or suspended in a liquid carrier, such as water, vegetable oil, alcohol, polyethylene glycol, propylene glycol or glycerin. Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain viscosity enhancing agents to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethy[iota]cellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste. Preservatives and chelating agents such as alcohol, sodium benzoate, butylated hydroxy toluene, butylated hydroxyanisole and ethylenediamine tetraacetic acid can be added at safe levels to improve storage stability.

A liquid composition according to the present invention can also contain a buffer such as guconic acid, lactic acid, citric acid or acetic acid, sodium guconate, sodium lactate, sodium citrate or sodium acetate.

A composition for tableting or capsule filling can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting. A capsule filling of the present invention can comprise any of the aforementioned blends and granulates that were described with reference to tableting, only they are not subjected to a final tableting step.

A specific aspect of this invention is a method for preparing a pharmaceutical formulation as defined in claim 1, said method comprising dispersing corn starch in cold water (e.g. 5-20° C.), heating the mixture to form a paste, cooling the mixture to about 40-60° C. (e.g. 50° C.) to form a first composition; mixing ezetimibe, lactose monohydrate and corn starch to form a second composition; granulating said first composition together with said second composition, screening and/or milling the granules if necessary, drying the granules, screening the dried granules through an appropriate mesh if necessary, mixing the resulting composition with magnesium stearate, compressing the blend to appropriate size and weight on a suitable tabletting machine or filling into suitable capsules.

When preparing a composition comprising starch paste, 1 part of corn starch may be dispersed in about 1 to about 20 parts of cold water, preferably in about 2 to about 10 parts of cold water, more preferably in about 3 to about 8 parts of cold water, most preferably in about 4 to about 6 parts of cold water, e.g. in about 5 parts of cold water. It has been found that the dissolution characteristics are improved when less than 10 parts of cold water are used for preparing the corn starch paste.

It is therefore an aspect of this invention to use corn starch paste for the manufacture of a pharmaceutical composition as described herein, wherein said corn starch paste has a concentration of more than 10% by weight, preferably in water. Preferably, the concentration of corn starch in the paste is 11 wt-% to 30 wt-%, more preferably 15 wt-% to 20 wt-%, most preferably 16 wt-% to 18 wt-%.

The compositions and therapeutic combinations of the present invention can be administered to a mammal in need of such treatment in a therapeutically effective amount to treat one or more conditions, for example vascular conditions such as atherosclerosis, hyperlipidaemia (including but not limited to hypercholesterolemia, hypertriglyceridaemia, sitosterolemia), vascular inflammation, stroke, diabetes, obesity, and/or reduce the level of sterol (s) in the plasma. The compositions and treatments can be administered by any suitable means which produce contact of these compounds with the site of action in the body, for example in the plasma, liver or small intestine of a mammal or human.

The compositions of the present invention can be administered in any conventional dosage form, preferably an oral dosage form such as a capsule, tablet, powder, cachet, suspension or solution. The formulations and pharmaceutical compositions can be prepared using conventional pharmaceutically acceptable and conventional techniques. Several examples of preparation of dosage formulations are provided below. The pharmaceutical compositions can be administered, for example, as tablets, pills, powders, liquids, suspensions, emulsions, granules, capsules, suppositories, injection preparations (solutions and suspensions), and the like.

The dosage of a pharmaceutical composition for reducing cholesterol according to the present invention will depend on the method of use, the age, sex, weight and condition of the patient. Typically, about 1 mg to 200 mg of ezetimibe may be contained in an administration unit form, preferably a 10 mg tablet. The daily dosage for the various compositions and therapeutic combinations described above can be administered to a patient in a single dose or in multiple subdoses, as desired. Subdoses can be administered 2 to 6 times per day, for example. Preferably, the pharmaceutical composition of the invention is administered once per day.

Having described the invention with reference to certain preferred embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Comparative Example

Formulation According to Example A of WO95/08532 or WO95/35277

| No. | Ingredient | mg/tablet |
|---|---|---|
| 1 | Active Compound | 100 |
| 2 | Lactose USP | 122 |
| 3 | Corn Starch, Food Grade, as a 10% paste in purified water | 30 |
| 4 | Corn starch, Food Grade | 45 |
| 5 | Magnesium stearate | 3 |
|  | Total | 300 |

Method of Manufacture:

Mix item No. 1 and 2 in suitable mixture for 10-15 minutes. Granulate the mixture with item No. 3. Mill the damp granules through a coarce screen (e.g., ¼", 0.63 cm) if necessary. Dry the damp granules. Screen the dried granules if necessary and mix with item No. 4 and mix for 10-15 minutes. Add item No. 5 and mix for 1-3 minutes. Compress the mixture to appropriate size and weight on a suitable tablet machine.

Example 1

| No. | Ingredient | Weight percent (mg) |
|---|---|---|
| 1 | Ezetimibe | 10 |
| 2 | Lactose monohydrate | 71 |
| 3 | Corn starch | 15 |
| 4 | Corn starch, Food Grade, as a paste in purified water | 3 |
| 5 | Purified water | Qs |
| 6 | Magnesium stearate | 1 |
|  | Total tablet weight | 100 |

Method of Manufacture:

Corn starch was dispersed in cold water (1 part corn starch to 8 parts water). The mixture was heated to about 95° C. form paste and cooled to about 50° C. Ezetimibe lactose and cornstarch were mixed and granulated using corn starch paste. Wet granules were dried at about 50° C., passed through #18 mesh screen and blended with magnesium stearate. The blend was compressed to appropriate size (Punch size 8×5.5 mm) and weight on a suitable tablet machine.

Formulations were prepared with the different samples of ezetimibe described in Example 5 infra.

Example 2

Dissolution Profile a) The Formulations according to Example 1 and the Comparative Example were evaluated to determine the dissolution rate using USP standard apparatus. Dissolution rate was determined by immersing each tablet in a solution of 500 ml of 1% sodium lauryl sulfate in a pH 4.5 phosphate buffer. The solution was constantly stirred using a paddle at a rate of 50 rpm. The results are reported below.

| | Percentage Active compound released | | | |
|---|---|---|---|---|
| Min | Example 1 (Sample 1 of Example 5a) | Comparative Example | Example 1 (Sample 2 of Example 5b) | Example 1* (Sample 2 of Example 5b) |
| 5 | 77.9 | 28.2 | 55.2 | 57.12 |
| 10 | 92.6 | 35.3 | 75 | 72.76 |
| 15 |  |  | 85.3 | 81.22 |
| 20 | 98.3 | 44.8 | 91.4 | 86.33 |
| 30 | 102.5 | 49.4 | 93.4 | 91.51 |
| 45 | 104 | 54.4 | 94.8 | 97.64 |

*Different dissolution medium: 0.01M sodium phosphate buffer pH 7 + 0.5% SLS 50 rpm, 900 ml Example 3

Formulation According to the Present Invention

| No. | Ingredient | Weight percent (mg) |
|---|---|---|
| 1 | Ezetimibe | 10 |
| 2 | Lactose monohydrate | 71 |
| 3 | Corn starch | 13 |
| 4 | Corn starch paste using 5 parts | 5 |

| No. | Ingredient | Weight percent (mg) |
|---|---|---|
|  | of purified water |  |
| 5 | Magnesium stearate | 1 |
|  | Total tablet weight | 100 |

Method of Manufacture:

Item No. 4 disperse in cold water (1 part corn starch to 5 parts water). Heat the mixture to about 95° C. to form paste and cool to about 50° C. Mix item No. 1, 2 and 3 in suitable mixer for 10 to 15 minutes and granulate with corn starch paste. Mill the damp granules from coarce screen if necessary. Dry the damp granules. Screen the dried granules through appropriate mesh (#30 mesh) if necessary and mix with item No. 5 for 3-5 minutes. Compress the blend to appropriate size and weight on suitable tablet machine or filled into suitable hard gelatine capsules on suitable encapsulating machine.

Dissolution rate at 30 minutes of the example 3 tablets showed more than 90% drug release therefore by increase in paste quantity and reducing the water quantity as state of art can be used to improve processes related issues without affecting the drug release.

Example 4

Formulation According to the Present Invention

| No. | Ingredient | Weight percent (mg) |
|---|---|---|
| 1 | Ezetimibe | 10 |
| 2 | Lactose monohydrate | 51 |
| 3 | Microcrystalline cellulose | 20 |
| 4 | Corn starch | 13 |
| 5 | Corn starch paste using 5 parts of purified water | 5 |
| 6 | Magnesium stearate | 1 |
|  | Total tablet weight | 100 |

Method of Manufacture:

Item No. 5 disperse in cold water (1 part corn starch to 5 parts water). Heat the mixture to about 95° C. to form paste and cool to about 50° C. Mix item No. 1, 2, 3 and 4 in suitable mixer for 10 to 15 minutes and granulate with corn starch paste. Mill the damp granules from coarce screen if necessary, dry the damp granules. Screen the dried granules through appropriate mesh (#30 mesh) if necessary and mix with item No. 5 for 3-5 minutes. Compress the blend to appropriate size and weight on suitable tablet machine or filled into suitable hard gelatine capsules on suitable encapsulating machine.

Example 5

Particle Size Measurement a) Particle Size Determination According to "Dry Powder Method".
Typical Instrumental Conditions:

| A) Instrument: | Malvern particle size Analyzer "Master sizer S" |
|---|---|
| B) Range lens: | 300 mm |
| C) Beam Length: | 10 mm |
| D) Sampler: | MS-64 |
| E) Presentation: | 3RHA |
| F) Analysis Model: | Compressed range |
| G) Obscuration range: | 15-30% |
| H) Feed rate: | ~30% |
| I) Air pressure: | 2.0 bar |

Procedure:

Pour the small volume sample in Drypowder Sampler unit. Set the feed rate & air pressure with the help of adjustable knob. And start the measurement until to get the obscuration between 15 and 30. Pass the laser beam through the sample cell to measure the particle size distribution and record the data into a histogram then report the results at 10%, 50% and 90% level of particles size distribution.

Note: Ensure the Laser power should be more than 60%.

Particle Sizes Determined for the Ezetimibe Used in Examples 1, 3 and 4:

| Sample No. | d(0.1) | d(0.5) | d(0.9) |
|---|---|---|---|
| 1 | 3.946 | 7.926 | 16.810 |
| 2 | 3.199 | 6.156 | 11.394 |
| 3 | 3.349 | 6.356 | 11.429 | b) Particle Size Determination According to "Wet Method".
Ezetimibe Samples PSD Measurement by Malvern Laser Diffraction A Malvern Laser Diffraction instrument was used to characterize the particle size distribution of ezetimibe. A Mastersizer S model equipped with a small cell dispersion unit MSI with a digital dispersion unit controller was used. The measurement was done using range lens 300RF (working range 0.05-900 mem), beam length: 2.40 mm and presentation 3NHE. In this case, a solution of dioctyl sulfosuccinate sodium salt in n-hexane was used as a dilution medium. The measurement was started after 1 minute of recirculation after suspension addition into measurement cell at speed rate 2000+−10 rpm. The suspension was prepared of ~0.1 g sample in solution 0.065% dioctyl sulfosuccinate sodium salt in n-hexane by vortex for 10 seconds and by sonication for 30 seconds. According to the accepted rules of Good Manufacture Procedures, the sample of ezetimibe is preferably measured after a successful blank measurement (% obscuration NMT 0.1%) is performed.

Results are given below.

Particle Sizes Determined for the Ezetimibe Used in Example 1:

| Sample No. | d(0.1) | d(0.5) | d(0.9) |
|---|---|---|---|
| 1 | 4.424 μm | 12.769 μm | 38.333 μm |
| 2 | 8.5 μm | 20.8 μm | 61.2 μm |

Particle Sizes of Further Ezetimibe Samples According to the Invention, Measured According to the "Wet Method":

| Sample No. | d(0.1) | d(0.5) | d(0.9) |
|---|---|---|---|
| 4 | 2.02 μm | 4.11 μm | 8.21 μm |
| 5 | 2.70 μm | 6.76 μm | 16.47 μm |

Example 6

Determination of Specific Surface Area

Method of Analysis
Specific surface area is measured by using the following Parameters:
Instrument: Pulse Chemisorbs 2700 (micromeritics)
Degassing: With out degassing
Sensitivity: No
Calculations: BET
Type: Single point system
Points: One
Sample cell: 6 cm$^3$
Procedure:
Sample no. 1 of example 5b) of known weight is taken in the sample transparent U shape glass tube. The sample is preheated to remove all atmosphere at liquid nitrogen temperature (−196° C.). This is achieved by passing nitrogen through the sample tube, which is placed in a liquid nitrogen bath (−196° C.). The value divided by the weight of the catalyst/sample taken in the tube gives the surface area of the sample.

BET Surface Area:
Surface area determination is an important factor in determining the catalyst performance, a method of assessing the efficiency of the catalyst support and promoter. The surface area measurement can be used to predict catalyst poisoning and provide reasons for the deactivation of the catalyst either due to poisoning or due to sintering. The BET (Brunner, Emmett and Teller) equation is based on the extension of Langmuir theory to multilayer. The basic equation to find the surface area is follows $$P/[V_{ads}(P_0-P)]=1/V_mC+[(C-1)P]/(V_mCP_0)$$

Where
P=Equilibrium adsorption pressure
P$_0$=Saturated vapour pressure of the adsorbent
V$_{ads}$=Volume (in ml) adsorbed at STP at pressure P
V$_m$=Volume of adsorbate required to form a monolayer cocerage
C=Constant related to heat of adsorption
According to BET method a plot of $$P/[V_{ads}(P_0-P)] \text{ Vs } P/P_0$$

Is a straight line (in the range of P/P$_0$:0.05-0.3) with slope (C−1)/(V$_m$C) and intercept 1/V$_m$C. By knowing these intercept and slope values calculated and further specific surface area can be calculated as follows Specific surface area (m$^2$/g)={[$Vm \times N_A$]/[22414×Wt]}×$A_m$ Where,
Vm=monolayer volume in ml at STP
N$_A$=Avogadro number
Wt=Weight of the catalyst
A$_m$=mean cross sectional area of adsorbate molecule (0.162 nm$^3$ for N$_2$)

Specific surface area of ezetimibe is 1.24 m$^2$/gram.

Example 7

Further Formulations According to the Present Invention

| Ingredients | mg/tablet | Ingredients | mg/tablet | Ingredients | mg/tablet |
|---|---|---|---|---|---|
| Ezetimibe | 10.0 | Ezetimibe | 10.0 | Ezetimibe | 10.0 |
| Lactose monohydrate | 65.0 | Microcelac | 80.0 | Mannitol (perlitol ® 160C) | 60.0 |
| Meglumine | 5.0 | Sodium Lauryl Sulphate | 2.0 | Avicel ® 101 | 20.0 |
| Polacrilline potassium | 4.0 | Polyplasdone XL10 | 4.0 | Polacrilline potassium | 4.0 |
| Sodium Lauryl Sulphate | 2.0 | Copovidone | 3.0 | Sodium Lauryl Sulphate | 2.0 |
| Copovidone | 3.0 | Purified water | Qs | Copovidone | 3.0 |
| Purified water | Qs | Magnesium stearate | 1.0 | Purified water | Qs |
| Lactose DCL11 | 10.0 | TABLET WEIGHT | 100.0 | Magnesium stearate | 1.0 |
| Magnesium stearate | 1.0 | | | TABLET WEIGHT | 100.0 |
| TABLET WEIGHT | 100.0 | | | | |

The invention claimed is:

1. A pharmaceutical composition comprising:
   5 to 20 wt-% ezetimibe particles (1-(4-fluorophenyl)-3(R)-[3-(4-fluorophenyl)-3(S)-hydroxypropyl]-4(S)-(4-hydroxyphenyl)-2-azetidinone),
   50 to 85 wt-% diluent,
   3 to 25 wt-% disintegrant,
   2 to 5 wt-% solubility enhancer
   1 to 10 wt-% binder, and
   0.5 to 1 wt-% lubricant,
   wherein the ezetimibe particles have a particle size distribution characterized by a d(0.9) value of 9 μm to 20 μm and a d(0.5) value of 3 μm to 50 μm.

2. The pharmaceutical composition according to claim 1, wherein the d(0.5) value for the ezetimibe particles ranges from 4 μm to 10 μm.

3. The pharmaceutical composition according to claim 1, wherein the specific surface area of the ezetimibe particles is less than 5 m$^2$/g.

4. The pharmaceutical composition according to claim 3, wherein the specific surface area of the ezetimibe particles ranges from 1 m$^2$/g to 1.5 m$^2$/g.

5. The pharmaceutical composition according to claim 1, wherein the composition has a dissolution profile such that at least 90% of the ezetimibe particles are released within 30 minutes.

6. The pharmaceutical composition according to claim 1, wherein the binder is a corn starch paste comprising more than 10% by weight in water.

7. The pharmaceutical composition according to claim 1, wherein the composition comprises 9 to 11 wt-% ezetimibe particles.

8. The pharmaceutical composition according to claim 1, wherein the composition comprises 60 to 80 wt-% diluent.

9. The pharmaceutical composition according to claim 1, wherein said diluent is selected from the group consisting of lactose monohydrate, spray dried lactose, mannitol, microcrystalline cellulose and combinations thereof.

10. The pharmaceutical composition according to claim 1, wherein the composition comprises 10 to 15 wt-% disintegrant.

11. The pharmaceutical composition according to claim 1, wherein said disintegrant is selected from the group consisting of corn starch, polyvinyl polypyrrolidone, polacrillin potassium and combinations thereof.

12. The pharmaceutical composition according to claim 1, wherein the composition comprises 4 to 6 wt-% binder.

13. The pharmaceutical composition according to claim 1, wherein said binder is corn starch paste and/or copovidone.

14. The pharmaceutical composition according to claim 1, wherein said lubricant is magnesium stearate.

15. The pharmaceutical composition according to claim 1, wherein said solubility enhancer is selected from the group consisting of meglumine, sodium lauryl sulphate and combinations thereof.

16. The pharmaceutical composition according to claim 1, wherein said composition is formulated as a tablet exhibiting a hardness of 20 N to 70 N.

17. The pharmaceutical composition according to claim 1, wherein said composition has a disintegration time of less than 120 seconds.

18. The pharmaceutical composition according to claim 1, wherein said composition further comprises:
    10 wt-% ezetimibe particles;
    71 wt-% lactose monohydrate;
    13 wt-% corn starch;
    5 wt-% corn starch paste; and
    1 wt-% magnesium stearate.

19. A method for preparation of the pharmaceutical composition according to claim 1, the method comprising the steps of:
   a) providing particles of ezetimibe (1-(4-fluorophenyl)-3(R)-[3-(4-fluorophenyl)-3(S)-hydroxypropyl]-4(S)-(4-hydroxyphenyl)-2-azetidinone), said particles having a particle size distribution characterized by a d(0.9) value of 9 μm to 20 μm and a d(0.5) value of 3 μm to 50 μm and a specific surface area of less than 5 $m^2/g$;
   b) preparing a blend comprising said ezetimibe particles and the following pharmaceutically acceptable excipients: 50 to 85 wt-% diluent, 3 to 25 wt-% disintegrant, 2 to 5 wt-% solubility enhancer 1 to 10 wt-% binder, and 0.5 to 1 wt-% lubricant,
   c) optionally granulating the blend; and
   d) processing the blend into a pharmaceutical composition, wherein the pharmaceutical composition comprising 5 to 20 wt-% ezetimibe particles.

20. The method according to claim 19, wherein the blend is granulated with a granulating fluid.

21. The method according to claim 20, wherein the granulation step comprises roller compaction.

22. The method according to claim 19, wherein the blend of step (b) is directly compressed into tablets.

23. The method according to claim 19, further comprising the steps of:
   dispersing a binder excipient comprising corn starch in cold water to form a first mixture,
   heating the first mixture to form a corn starch paste,
   cooling the corn starch paste to a temperature of 40 to 60° C.,
   mixing the ezetimibe particles with a diluent comprising lactose and a binder comprising corn starch to form a second mixture,
   granulating the second mixture using the corn starch paste,
   drying the granules,
   blending the granules with lubricant magnesium stearate and
   compressing the granules on a suitable tabletting machine or encapsulating the granules into capsules.

24. The method according to claim 19, further comprising the steps of:
   dispersing 1 part of corn starch in 3 to 8 parts of water,
   heating the dispersion to form a paste, and
   cooling the mixture.

* * * * *